United States Patent [19]

McRae

[11] Plant 5,005

[45] Mar. 22, 1983

[54] LILY PLANT: LILIUM HARVEST

[75] Inventor: Edward A. McRae, Boring, Oreg.

[73] Assignee: Melridge, Inc., Sandy, Oreg.

[21] Appl. No.: 200,967

[22] Filed: Oct. 27, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant bearing large clusters of medium sized flowers of excellent form, unusual color, and long persistence, both on the plant and as cut flowers. The plant is characterized by rapid natural propagation under field conditions and vigorous and healthy growth when forced under glass. It is further characterized by uniform growth to maturity when forced into flower throughout the year. The buds are exceptionally large and bright colored. The flowers are broad and thick petaled and of an intense bright orange color.

1 Drawing Figure

BACKGROUND AND GENERAL STATEMENT OF THE INVENTION

My new variety of lily is classified botanically as a Lilium hybrid; commercially, as an upright Asiatic hybrid, division I-A in the Horticultural classification of the Genus Lilium adopted by The Royal Horticultural Society of London.

My new variety of lily plant originated as a seedling selected from a group of seedlings among the seedling beds of test crosses of Oregon Bulb Farms at Sandy, Oreg. The cross was made in 1968 and the lily plant first flowered in 1970.

The cross was made during a breeding program having as its objective the production of brilliantly-colored, upright flowering lily cultivars which would perform well when forced into flower under glass throughout the year, in addition to meeting the requirements of vigor, disease resistance and rapid natural propagation under field cultivation. Cultivars were sought which would be disease resistant, virus tolerant, and not overly susceptible to leaf scorch and bud abortion upon forcing under glass.

The cross was made between the seed parent 'Harmony' (not patented) and the pollen parent 'Red Carpet' (not patented).

My new lily plant is characterized by rapid natural propagation under field conditions and by vigorous and healthy growth when forced under glass without excessive leaf scorch and bud abortion. It shows the uniform qualities of growth to maturity when forced into flower throughout the year. Its buds are exceptionally large and bright orange in color.

The flowers of my new lily plant are particularly distinctive. They are characterized by the exceptional breadth and thickness of the tepals and by their intense bright orange color.

Lilium 'Harvest' most closely resembles the older cultivar 'Harmony', which is its seed parent. However, it differs from it, and is superior to it, in its more intense orange color, its exceptionally large and bright orange colored buds, and by its broader and thicker-petaled orange flowers. When forced under glass, it shows uniformly good performance in that its flowers all bloom at approximately the same time.

My new variety of lily plant has been asexually reproduced by me and under my direction at Sandy, Oreg. Successive generations produced by bulb scale propagation and natural propagation from bulblets have demonstrated that the novel and distinctive characteristics of my new variety are fixed and hold true under asexually propagation from generation to generation.

THE DRAWING

My new variety of lily plant is illustrated on the accompanying photographic drawing which shows the plant, its foliage, and its buds in their various stages of development and the open bloom in full color.

DESCRIPTION OF THE NEW VARIETY

The following is a detailed description of my new variety of Asiatic hybrid lily, with nomenclature according to *The International Lily Register* (Royal Horticultural Society, London, 2nd edition, 1969) and with color designations according to The Royal Horticultural Society Colour Chart, published by The Royal Horticultural Society in 1966.

THE PLANT

Form: Bulbous monocotyledon.

Height: 60–75 cm (24–30") from bulbs 15–18 cm. in circumference.

Growth: Vigorous, with considerable strength.

Foliage: Abundant, about 80–100 leaves per stem.

*Size of leaves.*—6–9 cm. ($2\frac{1}{2}$–$3\frac{1}{2}$") long and 1–2 cm. ($\frac{1}{2}$–1") wide.

*Shape of leaves.*—Broad lanceolate.

*Texture of leaves.*—Leaves entire, not serrated, glossy, smooth, and glabrous.

*Color of leaves, upperside.*—Deepest green.

*Color of leaves, underside.*—Deep green.

*Ribs and veins of leaves.*—Typical monocotyledonous venation: light green parallel veins.

Color of bulbs: White.

Size of bulbs: Usual commercial size is 12–20 cm. (5–8") in circumference; bulbs can be cultivated for a longer time to reach much larger sizes if desired.

INFLORESCENCE

Compact raceme with short pedicels and high bud count. Bulbs 12–15 cm. in circumference produce about 8 buds; bulbs 15–18 cm. in circumference produce about 10 buds.

No hairy peduncle or pedicel.

Strength of inflorescence: Strong and wirey.

Color of inflorescence: Stems are dark green; buds are brilliant orange.

THE BUDS

Size: 7–9 cm. (3–3½") long.

Form: Lanceolate with obtuse tip; typical or upright Asiatic hybrid lilies.

Opens slowly: Opens in about 1 hour in response to morning light; flowers which are further up the stem open on subsequent days over an interval of 1–2 weeks. Typical of upright Asiatic hybrid lilies.

Color of mature buds: Bright orange, R.H.S. CC #28B.

THE FLOWER

Blooms: Late June or early July in western Oregon, once, in midseason, and profusely.

Size:

Flower diameter.—15–18 cm. (6–7").

Inner tepals.—4–5 cm. (1½–2") wide.

Outer tepals.—3–4 (1¼–1½") wide.

Shape when flower first opens: Very shallow bowl-shape, with tepal tips recurving only slightly.

Tepals recurve slightly more as flower ages.

Tepal arrangement: Typical of the genus Lilium, with 6 entire, imbricated tepals.

*Color, outer tepal.*—Bright orange, Royal Horticultural Society of London's Color Code #28A. The illustrated color is less orange than the actual color, in view of the lighting conditions at the time the blossoms were photographed. The variety, Enchantment, shows the true orange color, but with less intensity.

*Color, base of tepals.*—Bright orange, R.H.S. CC #28A.

*Color, inner tepal.*—Bright orange, R.H.S. CC #28A.

*Color, reverse of tepals.*—Bright orange, R.H.S. CC #28B.

Tepals remain on individual flowers 5–7 days; stem has flowers with tepals adhering for about 3 weeks.

Flower texture: Shiny, velvety. Is not affected by hot or wet weather.

*Persistence.*—It does not hang on and dry; tepals fall as flower ages.

Pedicels: 5–10 cm. (2–4"). Sturdy and upright.

*Color.*—Deep green.

Disease resistance: To Botrytis blight and to Fusarium bulb rot.

Fragrance: None.

Lasting quality: Flowers remain on plant for about three to four weeks. Flowers remain on cut-flower stems for about three weeks, with adequate light.

REPRODUCTIVE ORGANS

Stamens and anthers: Typical of genus Lilium. 6 Versatile anthers hang (singly) from 6 filaments.

Filaments: 5–6 cm. (2") long and light orange.

Pollen: Bright orange-brown, R.H.S. CC #169A.

Pistil: 1, Typical of genus Lilium. Style is 5–6 cm. (2") long.

Stigma: Small, 3-lobed, purple in color, velvety in texture.

Ovary: Typical of genus Lilium. Superior, 6-chambered, single ovary.

THE FRUIT

Fruit: Fertile, an ovoid to oblong capsule with 6 chambers.

Color at maturity: Medium green overlaid (under cool conditions) with light purple; fades to soft brown when capsule splits open to release seeds.

I claim:

1. A new and distinctive variety of Asiatic hybrid lily plant substantially as herein shown and described, characterized by its rapid natural propagation under field conditions, vigorous and healthy growth when forced under glass, and a uniform growth to maturity when forced to flower throughout the year; by its exceptionally large bud size and bright orange bud color; by its broad and thick petaled flowers; and by the intense bright orange color of its flowers.

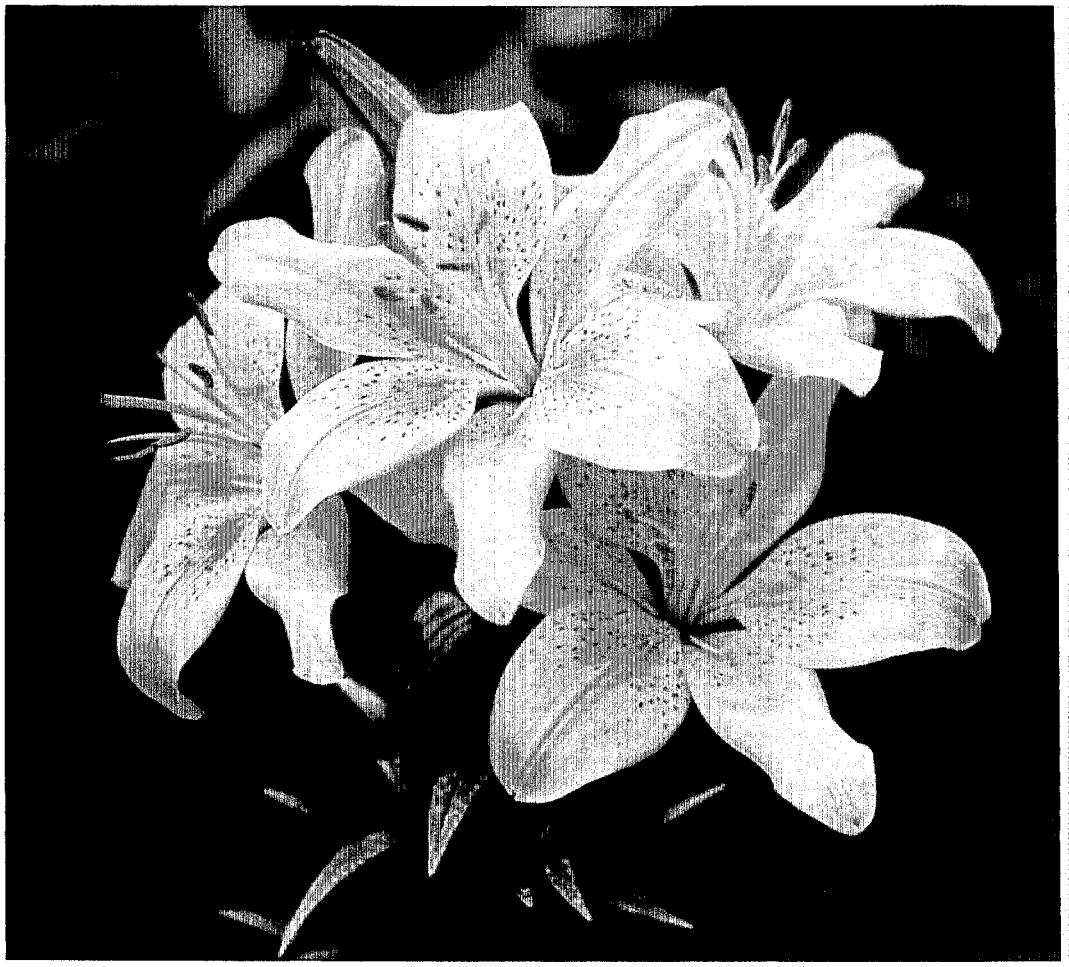

* * * * *